United States Patent [19]

Shafer

[11] Patent Number: 4,870,855

[45] Date of Patent: Oct. 3, 1989

[54] GAS SENSOR PROTECTION DEVICES AND ASSEMBLIES

[75] Inventor: J. Howard Shafer, Sunnyvale, Calif.

[73] Assignee: Delphian Corporation, Northvale, N.J.

[21] Appl. No.: 136,659

[22] Filed: Dec. 22, 1987

[51] Int. Cl.$^4$ .............................................. G01N 27/00
[52] U.S. Cl. .......................................... 73/23; 422/83
[58] Field of Search .................. 73/23, 27; 422/98, 83

[56] References Cited

U.S. PATENT DOCUMENTS

| | | | |
|---|---|---|---|
| 2,556,832 | 6/1951 | Vollrath | 73/27 R |
| 2,671,336 | 3/1954 | Hulsberg | 73/23 |
| 2,961,710 | 11/1960 | Stark | 264/54 |
| 3,025,200 | 3/1962 | Powers | 428/357 |
| 3,175,030 | 3/1965 | Green | 264/321 |
| 3,421,362 | 1/1969 | Schaeffer | 73/23 |
| 3,496,266 | 2/1970 | Fairbanks | 264/321 |
| 3,522,010 | 7/1970 | Archer | 73/23 |
| 3,622,435 | 11/1971 | Cacella | 428/288 |
| 3,661,267 | 5/1972 | Markley | 210/497.01 |
| 3,862,576 | 1/1975 | Pogorski | 73/23 |
| 3,890,100 | 6/1975 | Busch | 376/256 |
| 3,985,032 | 10/1976 | Avakian | 73/863.25 |
| 4,007,625 | 2/1977 | Houben et al. | 73/23 |
| 4,134,289 | 1/1979 | Boh et al. | 73/23 |
| 4,225,842 | 9/1980 | Schlesselman et al. | 422/98 |
| 4,352,286 | 10/1982 | Nakatani et al. | 73/23 |
| 4,386,269 | 5/1983 | Murphy | 340/605 |
| 4,476,706 | 10/1984 | Hadden | 73/1 G |

FOREIGN PATENT DOCUMENTS

| | | | |
|---|---|---|---|
| 172047 | 8/1986 | Japan | 73/23 |
| 693217 | 10/1979 | U.S.S.R. | 422/98 |
| 2067294 | 7/1981 | United Kingdom | 422/83 |

Primary Examiner—Hezron E. Williams
Attorney, Agent, or Firm—Fitch, Even, Tabin & Flannery

[57] ABSTRACT

Hazardous gas sensor assemblies having a reticulated foam splash guard, and reticulated foam splash guards for such hazardous gas assemblies.

6 Claims, 2 Drawing Sheets

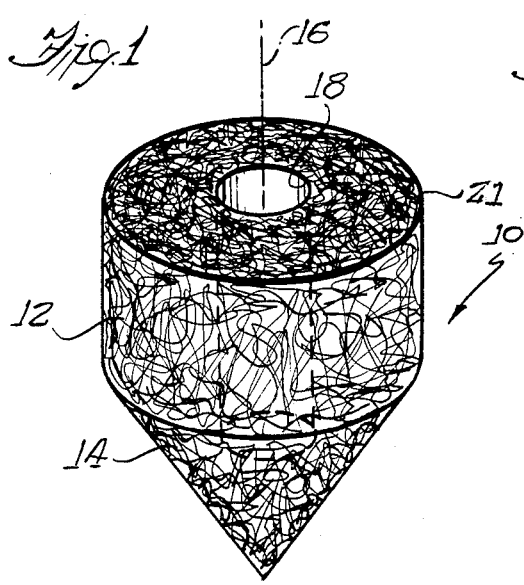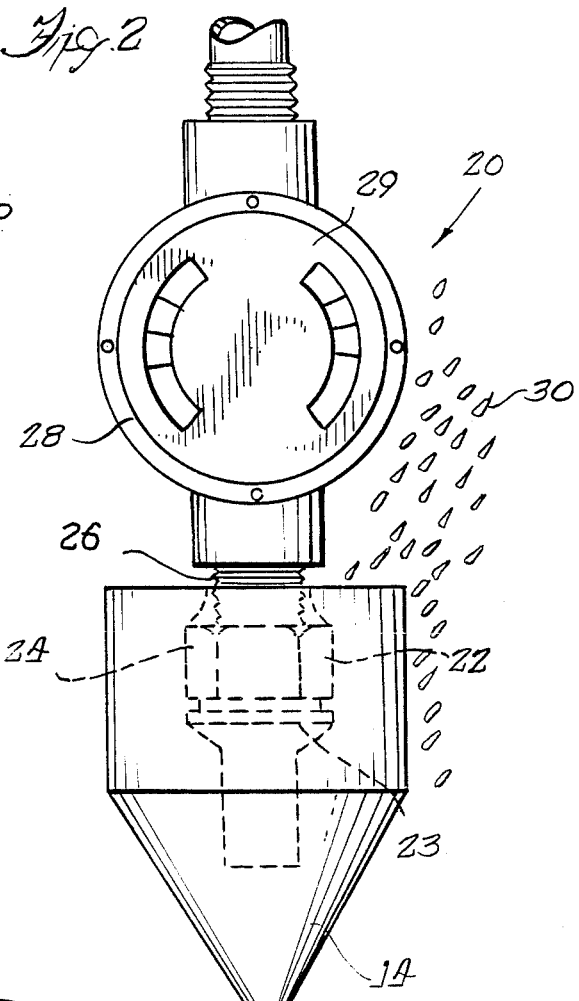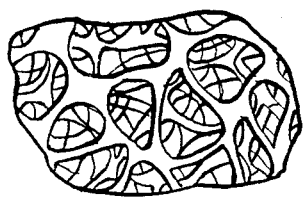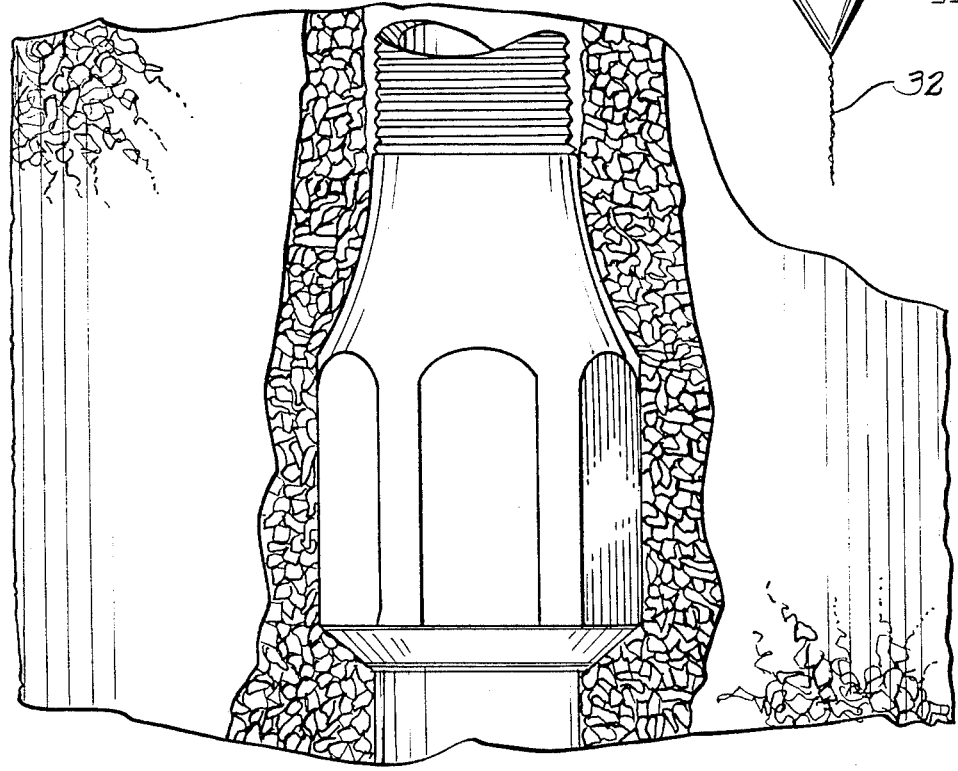

GAS SENSOR PROTECTION DEVICES AND ASSEMBLIES

BACKGROUND OF THE INVENTION

Generally, the present invention is directed to methods and apparatus for hazardous gas detection. More particularly, the present invention is directed to systems for detecting hazardous gases in inclement environmental conditions which may include conditions such as rain, and directed fluid streams such as splashed or hosed water.

In many types of gas-detection systems for hazardous gases, such as combustible hydrocarbons and hydrogen sulfide, hazardous gas sensors are positioned at locations at which hazardous gas monitoring is necessary or appropriate. Such sensors typically interpose a porous metal flame arrestor between electrical gas sensor elements and the environment, for safety purposes. An output or controller device may be combined with the sensor, or may be positioned remotely from the sensor for monitoring the sensor output. Such sensors are conventionally located in and around factories, pilot plants, refineries and chemical process plants, where they may be continuously or intermittently subjected to undesirable environmental operating conditions such as dust, dirt, rain and directed fluid streams. In this regard, water sprays, mists or streams from repair, maintenance or cleaning operations, as well as leakage, breakdown or faulty operation of equipment or manufacturing processes may adversely affect the performance and reliability of a hazardous gas sensor unless the sensor is protected from such conditions. Similarly, hazardous gas sensors which are located in unprotected outside areas will be exposed to rain and other adverse environmental conditions which may also degrade or defeat sensor performance. Excessive moisture can damage gas sensors by causing the sensor to short, by causing thermal shock to sensors operated at elevated temperatures, by combining with corrosive gases to chemically attack the sensor, and may interact with ambient dust or dirt to permanently plug up porous flame arrestors which will inhibit sensor performance. Of course, water alone will typically fill the pores of the flame arrestor of a hazardous gas sensor having such an arrestor, thereby at least temporarily inhibiting sensor performance until it is dried from the arrestor Moreover, hydrogen sulfide sensors are adversely affected by moisture, which can defeat or degrade sensor performance. As indicated, hazardous gas sensors should be protected from such excess moisture, which can temporarily or permanently interfere with the ability of such sensors to detect the presence, or measure the quantity of hazardous gas. However, because such sensors are intended to measure and detect hazardous gases, and because rapid sensor response to the environment is important for safety or process control reasons, it is important that sensor protective apparatus should not significantly interfere with free and ready access and exposure to the atmosphere in the zone to be protected by the sensor.

Typically, hazardous gas sensors are protected from fluid contamination or interference such as rain, splashed water or hosed water by protective splash guard devices made from a plurality of slotted tubes of varying diameters, arranged concentrically, with respective slots of adjacent consecutive tubes angularly displaced from each other, to present a cylindrical labyrinth passageway to water flow. Water entering the slots in an external tube may be deflected by the internally adjacent tube surface, and water passing through the internal tube slots may again be deflected by the next internally adjacent tube surface. Each deflection slows the water, so that it may drain from the bottom of the concentric tube splash guard before reaching the porous metal flame arrestor or hazardous gas sensor. However, conventional, concentric tubular splash guard devices may have a number of disadvantages. In this regard, if designed to permit rapid gas diffusion to the sensor, concentric tubular splash guard devices may not effectively keep water away from the sensor, and may be ineffective in protecting the sensor from water sprays or streams directed along the axes of the tubes. However, if such concentric slotted tube splash guard assemblies are designed to most effectively prevent water impingement on the sensor, the access of the sensor to the ambient atmosphere may be significantly impeded, and the time necessary for hazardous gas to diffuse around the labyrinth passageway to reach the sensor is increased, thereby increasing the time necessary for the sensor to be capable of detecting a hazard. Moreover, such concentric tube splash guard devices are typically designed to be screwed onto the sensor, which may present assembly or maintenance difficulties for hazardous gas sensors which are not positioned in readily accessible locations.

Accordingly, there is a need for improved hazardous gas sensor assemblies and sensor protection systems, and it is an object of the present invention to provide such improved hazardous gas sensor assemblies and sensor protection systems. These and other objects will be apparent from the following detailed description and the accompanying drawings.

DESCRIPTION OF THE DRAWINGS

FIG. 1 is a perspective view of an embodiment of a unitary, reticulated organopolymeric foam guard for a hazardous gas sensor in accordance with the present invention;

FIG. 2 is a side elevational view, partially in phantom, of the unitary reticulated foam guard in assembly with a hazardous gas sensor to provide an environmentally protected hazardous gas sensor system;

FIG. 3 is an enlarged view, partially broken away, of the uniform reticulated organopolymeric foam hazardous gas sensor guard of FIG. 1, in assembly with another embodiment of a hazardous gas sensor element to provide an environmentally protected hazardous gas sensor system;

FIG. 4 is an enlarged view of a portion of the unitary reticulated organopolymeric foam hazardous gas sensor guard of FIG. 1.

DESCRIPTION OF THE INVENTION

Figure 5:
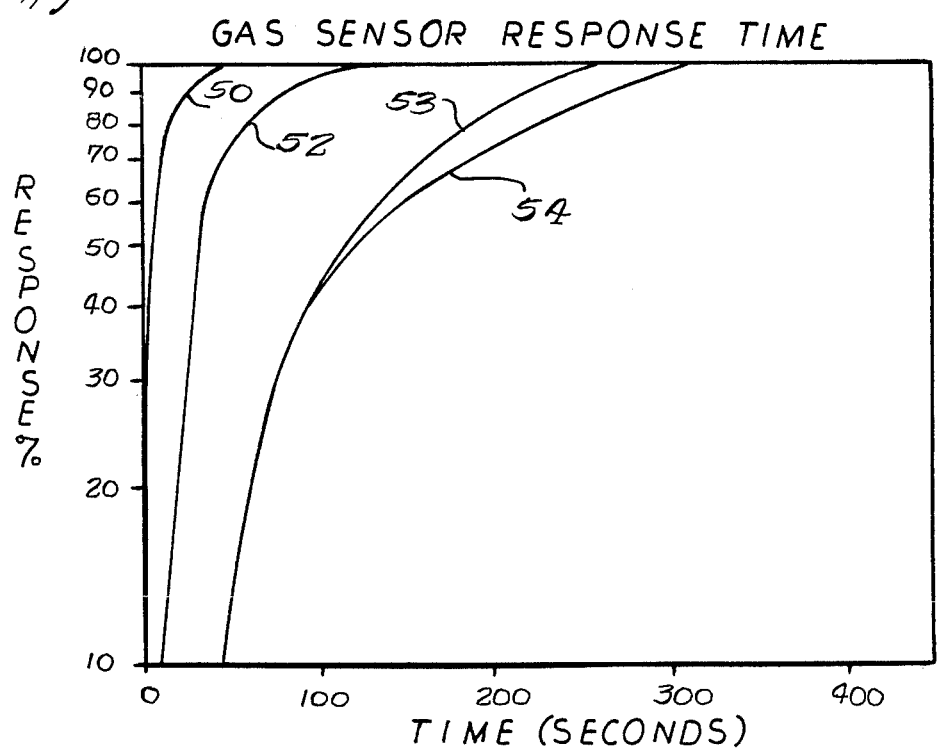
FIG. 5 is a graphical representation of sensor performance utilizing an embodiment of a unitary, reticulated organopolymeric foam for the sensor in accordance with the present invention.

Generally, the present invention is directed to hazardous gas sensor systems which are protected from environmental liquid contamination while providing a large plurality of gas diffusion pathways between the sensor and the ambient atmosphere for ambient hazardous gas detection. In accordance with the present invention, such protective hazardous gas sensor assemblies may comprise a hazardous gas sensor, which may be of conventional design, and a reticulated organopolymeric foam splash guard, which is desirably an organopolymeric foam, enclosing the hazardous gas sensor. Suitable hazardous gas sensors may be of conventional design comprising a sensor body containing hazardous gas detection means for detecting at least one hazardous gas, porous sampling means for enclosing the gas detection means within an enclosed sensor zone in the sensor body while permitting diffusive gas interchange between the enclosed sensor zone and the ambient atmosphere. The hazardous gas sensor will desirably have a predetermined external shape, which will typically be radially or rectilinearly symmetrical about an axis. The hazardous gas sensor body will typically have predetermined external dimensions, which will generally be within a range of from about 0.1 inch to about 3.0 inches, and preferably from about 0.5 to about 2 inches in width, and from about 0.25 to about 6 inches, and preferably from about 1.0 to about 4.0 inches in length. In operation, the porous sampling enclosure means will typically comprise a sintered metal plate positioned at the underside of the hazardous gas sensor so that the sensor projects downwardly from an electrical control box or other mechanical or electrical connection means. It is noted that moisture, particularly moisture containing dirt or dissolved solids, will adversely affect the sensor response and reliability.

The term organopolymeric includes polymers such as nylon and urethane, having backbone carbon groups, as well as polymers such as polysiloxanes having pendant carbon groups.

As indicated, further in accordance with the present invention, an organopolymeric, reticulated foam splash guard is provided which at least partially encloses the hazardous gas sensor body. The organopolymeric reticulated foam splash guard desirably may have a recess at its proximal end having a width less than that of the hazardous gas sensor body, and a depth sufficient to accommodate the sensor body. The organopolymeric, reticulated foam splash guard, in accordance with the present invention, should desirably have a minimum wall thickness of at least about 0.5 inch between the inner surface of the recess and the outer surface of the splash guard body, and preferably in the range of from about 0.75 inch to about 2.0 inches to provide adequate protection to the gas sensor from sprayed or splashed water. In addition, the body of the reticulated foam splash guard should desirably have a cross section which decreases in area in a direction toward its distal end to facilitate water removal by gravity. The guard should have a limited density of less than about 7.0 pounds per cubic foot and a pore size characterized by a pore density of from about 10 to about 100 pores per lineal inch and preferably from about 10 to about 50 pores per lineal inch. Particularly desirable results have been obtained with reticulated organopolymeric foam splash guards having a density of about 1.8 pounds per cubic feet and about 20 pores per lineal inch.

Reticulated open cell organopolymeric foams, which may be used to form a splash guard body in accordance with the present invention, have the form or appearance of a 3-dimensional knit, in which the open-celled zones ("pores") are interconnected or defined by fibers or filaments at the zones of cell intersection. Such reticulated foams have minimized cell wall surfaces and, accordingly, the splash guard body fabricated of such foam readily permits the diffusion of gas through the relatively thick splash guard body, from the environment to the gas sensor. However, the large number of fibers or filaments of the reticulated foam structure provided by the thick splash guard walls intercept directed water streams or rain, and protect the sensor as will be more fully explained hereinafter. The manufacture of open-cell, reticulated foams is well known in the art, such as described in U.S. Pat. Nos. 3,171,820; 3,175,025; 3,622,435; 3,496,266 and 3,025,200, which are incorporated herein by reference. Such reticulated foams may have a bulk density as low as one pound per cubic foot or less, or as high as about 7.0 pounds per cubic foot, and preferably in the range of from about 1.5 to about 7 pounds per cubic foot. Foamed organopolymeric cellular structures may, for example, be produced by expansion of gas bubbles within a polymer mass to form polyhedral cells. Foamed structures may desirably include cells of substantially uniform size and shape, but may also be formed by cells of varying shapes and sizes Through removal or rupture of the cell faces, a reticulated structure may be provided, having organopolymeric strands at the cell edges, but having substantially all of the cell walls removed to form pores which readily permit gas diffusion. The reticulated foam may be easily machined to form a splash guard in accordance with the present invention by means of a sharp knife or heated wire which cleanly severs the filaments without closing the pores at the machined surface. In accordance with preferred embodiments of the present invention, a splash guard is fabricated from a soft, resilient open-cell reticulated celloform structure having pores in the range of from about 15 to about 25 pores per lineal inch, and a density in the range of from about 1.5 to about 2.5 pounds per cubic foot. Preferably, the reticulated foam may be formed of an isocyanate-derived polymer such as a polyurethane polymer, or a nylon (polyamide) polymer. The reticulated organopolymeric celloform structure is a highly porous, integrally formed 3-dimensionally reticulated structure which is capable of intercepting a water stream, and diverting the stream under the force of gravity to drain from the splash guard structure, but which offers minimal impedance to the diffusion of ambient atmosphere through the reticulated pore structure to the hazardous gas sensor. The foam may be provided in substantially anisotropic configuration, so that splash guards may be provided which are substantially anisotropic in response to ambient atmospheric motion (e.g., air circulation direction) about the sensor enclosed by the splash guard. Isotropic foams, however, may be used, if desired.

The drainage of the water from the reticulated splash guard structure is facilitated by providing the splash guard with a decreasing cross sectional area, coming to a point at the bottom, or lowest point, of the splash guard in operational assembly with the hazardous gas sensor.

Having generally described the hazardous gas detector splash guard and splash protected sensor assembly of the present invention, the invention will now be more particularly described with reference to specific embodiments illustrated in FIGS. 1–4. In this regard, illustrated in FIG. 1 is an organopolymeric reticulated foam splash guard 10 comprising an upper cylindrical body 12 and a lower conical section 14. The illustrated device may be used to protect hazardous gas sensors from rain, splashed water and hosed water. It has been tested in all these conditions and has been found to function extremely well.

The splash guard 10 is radially symmetrical about a vertical axis 16, and is provided with a cylindrical recess 18 extending from the upper circular surface 21 along an axis 16 of rotational symmetry into the reticulated foam body 10. The upper surface 20 of the splash guard may have affixed thereto or coated thereon an impervious (e.g., plastic) surface or sheet as an additional protection if desired. The illustrated embodiment 10 is formed of a polyurethane foam having approximately 20 pores per lineal inch, ±5 pores per inch, and a density of approximately 1.8 pounds per square inch. The splash guard 10 is readily fabricated by use of a handsaw and coring blade, to provide the splash guard with open pored surfaces. In the illustrated, embodiment 10, the diameter of cylindrical section 12 of the organopolymeric reticulated foam splash guard is nominally 4 inches, and the diameter of the recess 18 is nominally 1 inch so that the minimum wall thickness of the splash guard is nominally about 1.5 inches. The height of the cylindrical section 12 is nominally 3 inches, and the height of the conical section 14 is also nominally 3 inches. The depth of the recess 18 within the reticulated foam body 10 is nominally about 3.5 inches.

The splash guard 10 of FIG. 1 is illustrated in assembly with a hazardous gas detector in FIG. 2 to provide an environmentally protected detector 20. The illustrated hazardous sensor is of a conventional design in which a porous combustible gas flame arrestor sensor sampling surface is exposed to the ambient atmosphere for monitoring of the environment. An explosion-proof terminal housing 28, which encloses circuitry for the operation of the combustible gas and reference sensor elements to provide a transmitter module 29, is shown in combination with the hazardous gas sensor body 24. The hazardous gas detector system of FIG. 2 comprises a conventional hazardous gas sensor element 22 comprising a hexagonally shaped sensor body 24, a threaded connector element 26 which is in threaded engagement with the epoxy-encapsulated transmitter module terminal housing 28. The transmitter module 28 may make electrical connection with a remote controller in accordance with conventional practice. The sensor element 22 is inserted within the recess 18 of the reticulated foam splash guard 10. The sensor body 24 projects downwardly from the housing 28, with the porous flame arrestor surface 23 being positioned at the underside of the sensor. The gas and reference sensor circuitry and housing therefor may be of conventional design, such as described in U.S. Pat. Nos. 4,305,724 or 4,476,706 which are hereby incorporated by reference. As shown in FIG. 2, the device comprises a sensor housing 22 which encloses a combustible gas sensor element and a matching reference element adapted for the catalytic combustion detection of combustible gas. The housing may be formed of any suitable material, and is conveniently machined from aluminum, steel or stainless steel bar stock to have a threaded base for assembly with the terminal box, and an upper cavity for containing the various sensor components. The catalytic gas sensor and reference elements are enclosed in a sensing zone defined by a gas-impermeable base plate, and the gas-permeable flame arrestor 23, such that combustible gas in the atmosphere surrounding the housing diffuses through the permeable metal flame arrestor for detection in the sensing zone. As indicated, the hexagonal body of the sensor element 22 has a diameter of 5.25 inches and a minimum width of 1.75 inches, which are each substantially greater than the diameter of the recess 18. Accordingly the resilient foam is stretched to accommodate the sensor element 22 and remains in compressive engagement therewith to retain the splash guard 10 in engagement with the sensor body. As illustrated in FIG. 2, raindrops 30 which strike the sensor assembly and are deflected by and entrapped within the reticulated foam network. Such deflections efficiently slow the water until gravity takes over and the water drains toward the point of the cone. The inverted cone shape reduces the surface area of the lowest part of the device, where the water could collect. This minimizes surface tension which could hold water in the device so that it drains rapidly and keeps water away from the sensor above it. The water drains from the bottom of the conical section 14 in a stream, away from the porous surface of the sensor element 22.

The sensor splash guard also serves as a dust guard, preventing contamination of the sensor from atmospheric dust. The guard may be readily cleaned by hosing or spraying with water or preferrably, by removal and water washing, without adversely affecting the sensor.

The illustrated splash guard has a large number of diffusion paths so that gas quickly reaches the sensor, but also has a large number of filament or deflector strands which not only stop water from reaching the active sensor surface, but which also guide the flow of water, under the force of gravity out of the splash guard and away from the sensor. The reticulated organopolymeric foam splash guard may be easily and conveniently assembled with conventional combustible gas sensor elements, by pushing over the sensor, a suitable unitary, resilient reticulated organopolymeric foam splash guard having a recess which is slightly smaller than the sensor. In summary, particularly desirable features of the protected system 20 of FIG. 2 include (1) multiple diffusion paths for fast response to hazardous gas, (2) effective multiple deflectors to stop water from reaching the sensor, (3) an inverted cone which minimizes forces holding water in the foam lattice and maximizes the drainage rate away from the sensor, and (4) ease of installation and use.

In tests of response to combustible gas, a sensor like that of FIG. 2, plus accessories, was saturated with 50% by volume of the lower flammability limit (LFL) of methane (CH4) inside an enclosure. The enclosure was removed and the sensor response signal was measured as a function of time from the time of removal of the enclosure. The time taken for the methane to escape from the sensor plus accessories when placed in a uniform, homogeneous air bath, is a measure of the time for a uniform, homogeneous methane mixture around sensor to get into the sensor. The sensor with the splash guard was found to have only slightly diminished response time in comparison to a sensor without the splash guard.

Similar tests were conducted with a hydrogen sulfide sensor, in which hydrogen sulfide was introduced at a predetermined time into an enclosed chamber containing the sensor and splash guard assembly, or the sensor alone. The response of the sensor with the splash guard was similarly found to be only slightly diminished from that of the sensor alone.

A typical response curve 50 for a hazardous gas sensor without a splash guard in comparison with the response 52 of the sensor with a reticular foam splash guard like that of FIG. 2, is shown in FIG. 5. The responses 53, 54 of two different baffle splash guards are also shown. The ability of the reticulated foam splash guards to protect the sensor from direct water spray was also tested by placing the sensor-splash guard assembly in a shower, and by directing hosed water at the sensor-splash guard assembly. No water reached the porous stainless steel flame arrestor of the sensor for either a 4 inch diameter foam sensor when in a shower for 2 minutes, or with high velocity garden hose for 1 minute. No water reached the flame arrestor for a 3 inch diameter foam splash guard in a shower for 2 minutes.

While the present invention has been specifically described with respect to specific embodiments of the invention, it will be appreciated that various modifications, variations and adaptations may be made within the spirit and scope of the present disclosure, which are intended to be within the scope of the following claims.

Various of the features of the invention are set forth in the following claims.

What is claimed is:

1. A hazardous gas sensor assembly comprising a hazardous gas sensor comprising a sensor body containing hazardous gas detection means for detecting at least one hazardous gas, and porous sampling means for enclosing the gas detection means within an enclosed sensor zone in the sensor body while permitting diffusive gas interchange between the enclosed sensor zone and the ambient atmosphere, said sensor body having a predetermined external shape, which is radially or rectilinearly symmetrical about the axis, and having external dimensions within a range of from about 0.1 inch to about 3.0 inches in width, and from about 0.25 to about 6 inches in length, and a reticulated foam splash guard at least partially enclosing the hazardous gas detector, said reticulated foam splash guard having a recess at its proximal end having a width less than that of the hazardous gas sensor body, and a depth sufficient to accommodate the sensor body, said reticulated foam splash guard having a minimum wall thickness of at least about 0.5 inch between the inner surface of the recess and the outer surface of the splash guard body and a limited density of less than about 7.0 pounds per cubic foot and a pore size characterized by a pore density of from about 10 to about 100 pores per lineal inch.

2. A hazardous gas sensor assembly in accordance with claim 1 wherein said reticulated foam splash guard is formed of a resilient organopolymeric reticulated foam.

3. A hazardous gas sensor assembly in accordance with claim 1 wherein said reticulated foam splash guard is formed of a metallic, carbon or ceramic reticulated foam.

4. A hazardous gas sensor assembly in accordance with claim 2 wherein the body of the reticulated foam splash guard has a cross section which decreases in cross sectional area below said sensor body in a direction toward its distal end to facilitate water removal by gravity.

5. A hazardous gas sensor assembly in accordance with claim 2 wherein said reticulated organopolymeric foam splash guard has a density of about 1.8 pounds per cubic feet and a pore density of about 20 pores per lineal inch.

6. A hazardous gas sensor assembly comprising a hazardous gas sensor comprising a sensor body containing hazardous gas detection means for detecting at least one hazardous gas, and porous sampling means for enclosing the gas detection means within an enclosed sensor zone in the sensor body while permitting diffusive gas interchange, between the enclosed sensor zone and the ambient atmosphere, said sensor body having a predetermined external shape, which is radially or rectilinearly symmetrical about the axis, and having external dimensions within a range of from about 0.1 inch to about 3.0 inches in width, and from about 0.25 to about 6 inches in length, and a three dimensional fiber network splash guard at least partially enclosing the hazardous gas detector having a recess at its proximal end having a width less than that of the hazardous gas sensor body, and a depth sufficient to accommodate the sensor body, said three dimensional fiber network splash guard having a minimum wall thickness of at least about 0.5 inch between the inner surface of the recess and the outer surface of the splash guard body and a limited density of less than about 7.0 pounds per cubic foot and a pore size characterized by a pore density of from about 10 to about 100 pores per lineal inch.

* * * * *